Figure 1:
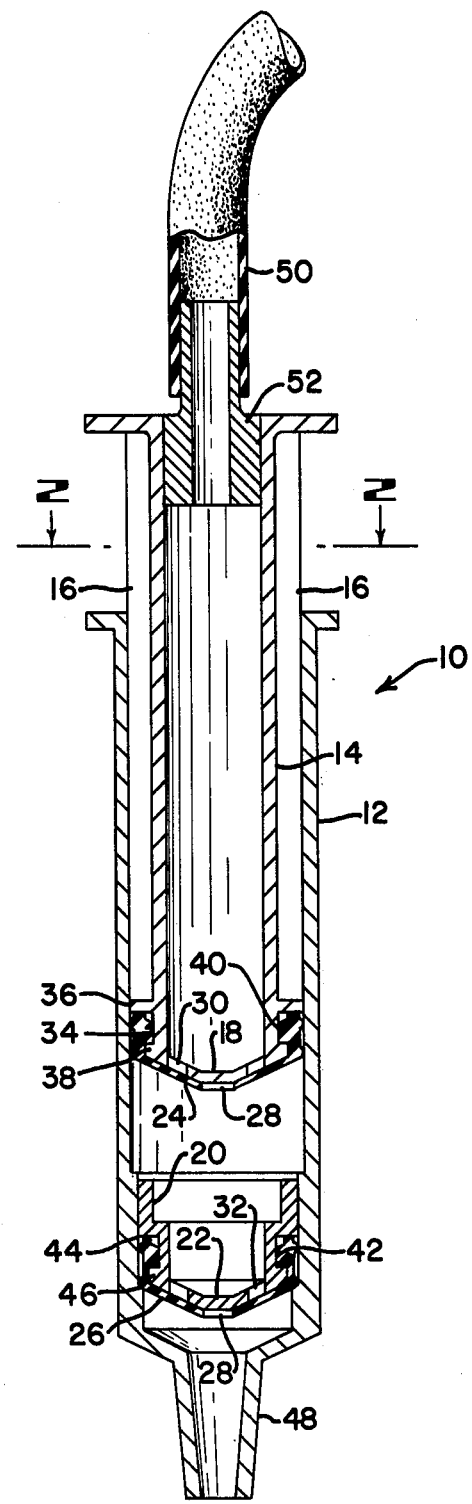

United States Patent [19]

Nye

[11] 4,153,186

[45] May 8, 1979

[54] VALVE AND MEDICANT DISPENSING SYRINGE

[75] Inventor: Norman H. Nye, Cuyahoga Falls, Ohio

[73] Assignee: Arthur T. Medkeff, Tallmadge, Ohio; a part interest

[21] Appl. No.: 817,142

[22] Filed: Jul. 20, 1977

[51] Int. Cl.² .......................................... A61M 5/315
[52] U.S. Cl. .................................. 222/378; 128/220; 137/853; 137/859; 222/380; 222/494
[58] Field of Search ........................... 128/218 M, 220; 137/853, 859; 222/378, 380, 383, 494, 207, 212

[56] References Cited

U.S. PATENT DOCUMENTS

| | | | |
|---|---|---|---|
| 1,367,008 | 2/1921 | Bessesen | 128/220 |
| 1,589,882 | 6/1926 | Hein | 128/220 |
| 3,342,208 | 9/1967 | Steffes | 137/853 X |
| 3,678,931 | 7/1972 | Cohen | 128/218 M |
| 3,685,514 | 8/1972 | Cheney | 128/218 M |

FOREIGN PATENT DOCUMENTS 2029179  4/1972  Fed. Rep. of Germany .......... 128/220

*Primary Examiner*—David A. Scherbel
*Attorney, Agent, or Firm*—Oldham, Oldham, Hudak & Weber Co.

[57] ABSTRACT

A dispensing syringe comprising telescopically engaged inner and outer sleeves or cylinders having corresponding dispensing ends and open receiving ends, an insert cup extends across and is positioned in the outer cylinder at its dispensing end, and a pair of identical resilient seal diaphragms engaging the outer surfaces of the dispensing end of the inner cylinder and of the insert cup for flow of material through the syringe in one direction. The seal diaphragms are of the same constructions for resilient engagement with the ends of the inner sleeve and the insert cup.

4 Claims, 2 Drawing Figures

U.S. Patent     May 8, 1979     4,153,186

VALVE AND MEDICANT DISPENSING SYRINGE

BACKGROUND OF INVENTION

In these days of high medical expenses and increasing costs for medicines, it is important that medicines be provided in unit forms available for convenient handling at the hospital and ease of dispensing medicines in these unit containers. Thus, efforts have been made heretofore to provide apparatus which has been proposed for filling cups or other containers with measured quantities of medicines to provide for convenient, inexpensive dispensing and handling of the medicines.

The present invention relates to an improved, relatively inexpensive positive acting device for processing materials, such as medicines, in a sanitary manner, and for dispensing measured quantities thereof into receiving containers or cups to fill a desired quantity of these containers with unit doses of the medicines. The dispensing syringe of the invention is relatively inexpensive and uncomplicated, whereby it can be discarded after one use thereof in filling, for example, from between about 50 to 200 or 300 of the carrier containers.

One prior type of a mechanism for dispensing a liquid is shown in U.S. Pat. No. 2,894,665, and it has a one-way valve means at a lower end of the measuring container and a float body that aids in forming a seal with the piston for expulsion of the liquid being processed. The apparatus of the present invention is much more positive in action and less complex in design than such patent. Another prior dispenser for viscous liquids is shown in U.S. Pat. No. 3,231,149, wherein an axially movable plunger is carried in a cylinder and a fixed closure valve and dispensing means is provided at the lower end of the container. But this is a particular structure differing materially from the compact uncomplicated apparatus of the present invention.

U.S. Pat. No. 2,894,665 also shows a typical apparatus with which the dispensing syringe of the invention can be used for being driven through a controlled cycle for efficiently measuring and dispensing a desired quantity of a liquid material.

The general object of the present invention is to provide an improved valve and dispensing unit, especially adapted for processing medicines and efficiently dispensing measured quantities thereof.

Other objects of the invention are to provide a one-way seal and valve means for use in a measuring and dispensing syringe or the like; and to secure a seal in a syringe by an edge bead on a resilient diaphragm seal.

Yet a further object of the invention is to provide two substantially identical valve and diaphragm seal members used in spaced axial relationship in a dispensing syringe for providing a low cost, reliable dispensing apparatus.

The foregoing and other objects and advantages of the invention will be made more apparent as the specification proceeds.

Figure 2:
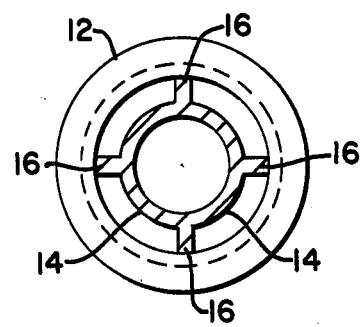

In the accompanying drawings,

FIG. 1 is a vertical section through a dispensing syringe, embodying the invention, having a supply tube connected thereto; and FIG. 2 is a horizontal section taken on line 2—2 of FIG. 1.

SUBJECT MATTER OF INVENTION

The dispensing syringe, as one embodiment of the invention, is made from a pair of plastic inner and outer sleeves that are telescopically engaged and have open receiving ends and an insert cup extending across and positioned in the outer sleeve adjacent its dispensing end, the outer sleeve having a dispensing end and the insert cup having a dispensing base or end and with the external contours of such dispensing ends being of the same general shapes and sizes and including an annular recess extending around the periphery of the end, and a pair of sealing diaphragms or means resiliently engaging the outer dispensing end of the inner sleeve and the dispensing end of the insert cup, the seal means having an edge rib securely received in said annular recess, such seal diaphragms each having a discharge hole on a center axis thereof and with the dispensing ends of said inner sleeve and said insert cup having openings therein offset from the center axis of the syringe whereby the resilient diaphragms normally retain the dispensing ends of the inner sleeve and of the insert cup closed but with dispensing pressure opening the diaphragm means for flow of material to be dispensed therethrough.

The syringe of the invention, as previously indicated, is adapted to be used in apparatus as shown in U.S. Pat. No. 2,894,665, but other unit dosage liquid and solid packaging machines have also been provided and are currently made in commercial models for rapidly and accurately loading desired quantities of a medicant into unit containers. This action can be provided by the dispensing syringe of the invention and have uniform quantities of materials passed through the apparatus in a sanitary manner.

Reference now is particularly directed to the structure shown in the drawings and wherein a dispensing syringe 10 is provided. This syringe 10 includes an outer sleeve or cylinder 12 and an inner sleeve or cylinder 14 telescopically engaged with and received in the outer cylinder 12. The inner sleeve preferably is provided with a plurality of axially directed circumferentially spaced ribs 16 provided at uniformly spaced portions around the periphery of the inner sleeve to guide the inner sleeve in the outer sleeve for axial reciprocation on the center axis of the syringe. Also, these ribs 16 aid in providing a radial space for attaching seal means to the inner sleeve 14 as hereinafter described.

The inner sleeve 14 has a normally closed dispensing end 18, and an insert cup 20 is also present and is received in the lower portion of the outer sleeve 12. This insert cup 20 also has a dispensing end or base portion 22 that is normally closed or sealed.

To aid in dispensing action and control of material being moved through the syringe of the invention, a pair of correspondingly shaped and sized resilient seal means, webs, or diaphragms 24 and 26 are provided one in engagement with the dispensing end 18 of the inner sleeve and the other in resilient engagement with the sealing end 22 or base of the insert cup 20. These seal diaphragms are provided with dispensing holes or openings 28 positioned on the axis of the syringe, while other dispensing openings 30 and 32 are formed in the dispensing end 18 and the base or end 22 of the cup and with such openings 30 and 32 being in offset axial relation to the openings 28 in the seal diaphragms. A plurality of these openings 30 and 32 can be provided in radially spaced relation to the openings 28. These seal diaphragms are tightly and resiliently positioned in engagement with the outer surfaces of the dispensing ends or bases of the members to which they are attached, and note that the lower end of the inner sleeve 14 has an annular recess 34 formed therein by adjacent substantially radially extending flanges 36 and 38. Thus, edge ribs or portions 40 on these seal diaphragms 24 and 26 are snugly received in and are resiliently retained in engagement with the associated portions of the dispensing syringe by these annular ribs 40 on the diaphragm, and by the shape and size of these seal diaphragms. A recess 42, corresponding to the recess 34, is formed in the outer periphery of the insert cup 20 by a shoulder 44 and a rib or flange 46 axially spaced therefrom and shorter in radial length than the shoulder 44 to be spaced from the outer sleeve to pass the web of the seal diaphragm between such insert cup and the adjacent surface of the outer cylinder or sleeve 12.

It will be noted that the outer sleeve 12 has a dispensing nozzle 48 formed at its lower end.

The drawing shows that a suitable supply tube 50 can be and is attached to the open upper receiving end of the inner sleeve 14 of the syringe. Usually some type of a connector fitting 52 is conventionally secured to the upper end of the inner sleeve 14 and engages the tube 50 to connect it to the syringe. Hence, any desired pump device or the like can be operatively connected to the syringe for supplying measured quantities of materials, usually liquid, to the syringe to be forced therethrough after the syringe has been filled with the material to be dispensed. Or, as shown in U.S. Pat. No. 2,894,665, the outer cylinder or sleeve 12 can be fixed to a suitable support and then the inner sleeve could be moved through operative cycles for dispensing measured quantities of material.

The valve or syringe of the invention has good operative properties, it is inexpensive, and it will dispense controlled quantities, as desired. Thus the objects of the specification have been met.

While one complete embodiment of the invention has been disclosed herein, it will be appreciated that modification of this particular embodiment of the invention may be resorted to without departing from the scope of the invention.

What is claimed is:

1. A dispensing syringe having an outlet and comprising an inner and an outer sleeve that are telescopically engaged and have corresponding dispensing ends and open receiving ends,
   a separate seal cup in and extending across the internal diameter of said outer sleeve and positioned in said outer sleeve adjacent its dispensing end, said seal cup having a dispensing end,
   a pair of resilient seal means individually engaging the outer surfaces of said dispensing end of said inner sleeve and of said seal cup for flow of material only towards the syringe outlet, said dispensing ends and seal means having openings therein offset in relation to each other, and the outer surfaces of the dispensing end of said seal cup and of said inner sleeve being of the same contour, said seal means being of the same size and configuration and tightly engaging said dispensing ends, a lower peripheral portion of said seal cup being spaced from said outer sleeve to receive an edge portion of a seal means.

2. A dispensing syringe comprising telescopically engaged inner and outer sleeves having corresponding dispensing ends and open receiving ends, said outer sleeve having a nozzle defining an outlet at its dispensing end,
   an insert cup positioned in said outer sleeve and extending across the internal diameter of said outer sleeve adjacent its dispensing end, said insert cup having a dispensing end and
   a pair of corresponding flexible seal means, of the same size and shape, tightly engaging the outer surfaces of said dispensing end of said inner sleeve and of said insert cup for flow of material only towards the syringe outlet, said dispensing ends having openings therein offset from the center axis of said sleeves, said seal means having an opening therein on the center axis of the syringe and closing said openings in said dispensing ends of said insert cup and said inner sleeve normally, but opening for flow of material towards said nozzle.

3. A dispensing syringe as in claim 2, where the outer surfaces of the dispensing end of said insert cup and of said inner sleeve are of the same contour and include an annular recess on side areas thereof, and said seal means each has an annular rib seated in its individual said recess to position said seal means and each has a seal web tightly extending over the outer surfaces of one of said dispensing ends, both of said annular ribs on said seal means being retained in position by said outer sleeve.

4. A dispensing syringe as in claim 2, where said outer sleeve has a radially inwardly extending thickened wall portion at the area thereof receiving said insert cup to facilitate positioning said insert cup and the said seal means thereon in said outer sleeve.

* * * * *